United States Patent
Lukin et al.

(10) Patent No.: US 9,809,534 B1
(45) Date of Patent: Nov. 7, 2017

(54) DIFLUOROALKYLCYCLOPROPYL AMINO ACIDS AND ESTERS, AND SYNTHESES THEREOF

(71) Applicant: AbbVie Inc., North Chicago, IL (US)

(72) Inventors: Kirill A. Lukin, Vernon Hills, IL (US); Jianzhang Mei, Lake Forest, IL (US); David R. Hill, Gurnee, IL (US); Michael J. Abrahamson, Chicago, IL (US)

(73) Assignee: AbbVie INC., North Chicago, IL (US)

( * ) Notice: Subject to any disclaimer, the term of this patent is extended or adjusted under 35 U.S.C. 154(b) by 0 days.

(21) Appl. No.: 14/802,392

(22) Filed: Jul. 17, 2015

Related U.S. Application Data

(60) Provisional application No. 62/026,854, filed on Jul. 21, 2014.

(51) Int. Cl.
| | |
|---|---|
| *C07C 271/24* | (2006.01) |
| *C07C 269/06* | (2006.01) |
| *C07C 69/74* | (2006.01) |
| *C07C 67/333* | (2006.01) |
| *C07C 67/347* | (2006.01) |
| *C12P 7/62* | (2006.01) |

(52) U.S. Cl.
CPC .......... *C07C 271/24* (2013.01); *C07C 67/333* (2013.01); *C07C 67/347* (2013.01); *C07C 69/74* (2013.01); *C07C 269/06* (2013.01); *C12P 7/62* (2013.01)

(58) Field of Classification Search
CPC ... C07C 271/24; C07C 67/333; C07C 67/347; C07C 69/74; C07C 269/06; C12P 7/62
See application file for complete search history.

(56) References Cited

FOREIGN PATENT DOCUMENTS

WO    WO2015100145    *   7/2015   ............... C07K 5/12

* cited by examiner

*Primary Examiner* — Paul A Zucker
*Assistant Examiner* — Mark Luderer
(74) *Attorney, Agent, or Firm* — Dana M. Gordon; Foley Hoag LLP

(57) ABSTRACT

The invention provides methods of synthesizing compounds in an asymmetric or enantioenriched fashion, wherein the compounds are useful intermediates in the synthesis of viral protease inhibitors.

15 Claims, No Drawings

DIFLUOROALKYLCYCLOPROPYL AMINO ACIDS AND ESTERS, AND SYNTHESES THEREOF

RELATED APPLICATIONS

This application claims the benefit of priority to U.S. Provisional Patent Application Ser. No. 62/026,854, filed Jul. 21, 2014, the contents of which are hereby incorporated by reference.

BACKGROUND

Complex biologically active molecules are challenging, expensive, and time-consuming to synthesize. Synthesizing chiral, non-racemic compounds with good enantio- and diastereoselectivity is even more challenging. An example of such a molecule is Compound 1:

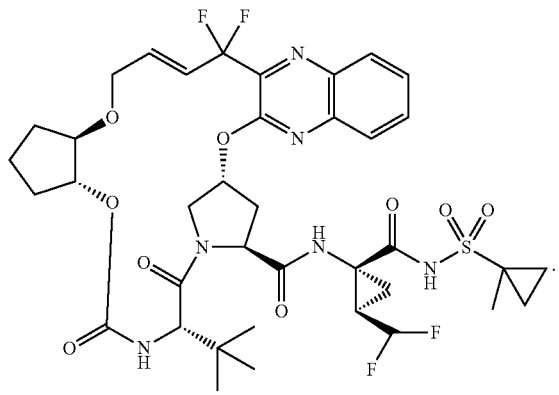 [SMILES: CC(C)(C)[C@@H]1NC(=O)O[C@@H]2CCC[C@H]2OC/C=C/C(F)(F)c2nc3ccccc3nc2O[C@@H]2C[C@@H](C(=O)N[C@]3(C(=O)NS(=O)(=O)C4(C)CC4)C[C@H]3C(F)F)N(C2)C1=O]

This compound is a potent inhibitor of the hepatitis C virus (HCV) NS3/4A protease; it shows broad genotype activity and substantially improved in vitro profile compared to earlier generation HCV NS3/4A protease inhibitors. While synthetic routes to this compound exist, the existing methods typically require, for example, high catalyst loading, dilute reaction conditions, and the use of expensive starting materials. Of particular interest is the difluoromethylcyclopropyl amino acid substituent. Previous synthetic methods relied upon corrosive fluorination chemistry to synthesize this feature; however, such fluorination reactions are difficult to adapt for large-scale production of Compound 1.

There exists a need for new synthetic methods to construct enantioenriched difluoroalkylcyclopropyl amino acids and esters.

SUMMARY OF THE INVENTION

In certain embodiments, the invention relates to a compound, or a salt thereof, having a structure selected from:

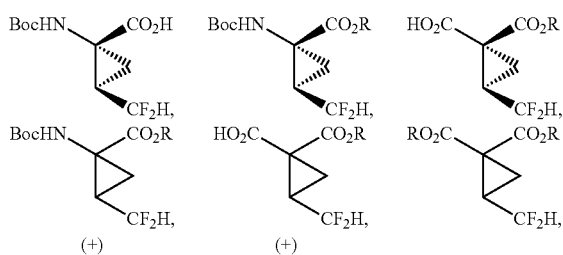

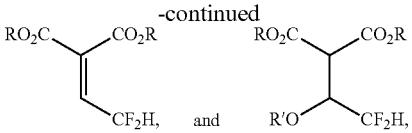

wherein, independently for each occurrence,
R is alkyl; and
R' is alkyl.

In certain embodiments, the invention relates to a hydrolysis method comprising:
contacting, in an eighth solvent, a compound of formula I with a fifth base, thereby forming a compound of formula J;
wherein
formula I is

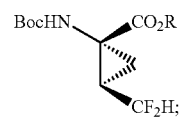

formula J is

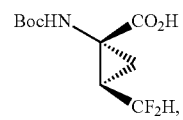

or a salt thereof; and
R is alkyl.

In certain embodiments, the invention relates to an enantioenrichment method comprising:
subjecting a compound of formula F to simulated moving bed chromatography, thereby obtaining the enantioenriched compound of formula I;
wherein
formula F is

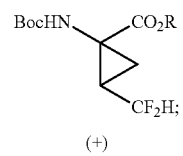

formula I is

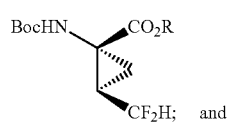

R is alkyl.

In certain embodiments, the invention relates to a method according to reaction scheme A:

Scheme A

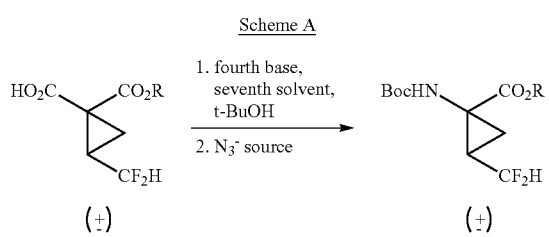

wherein R is alkyl.

In certain embodiments, the invention relates to a sequential selective hydrolysis method comprising:

selectively hydrolyzing with a first enzyme the 2S-enantiomer of a compound of formula D, thereby forming a fourteenth product mixture;

separating from the fourteenth product mixture an enantioenriched amount of the 2R-enantiomer of a compound of formula D, thereby forming a fifteenth product mixture comprising an enantioenriched compound of formula G;

regioselectively hydrolyzing with a second enzyme the compound of formula G, thereby forming a sixteenth product mixture comprising a compound of formula H,
wherein
formula D is

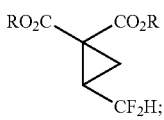

formula G is

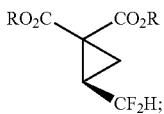

formula H is

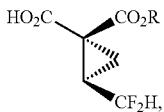

or a salt thereof; and
R is alkyl.

In certain embodiments, the invention relates to a method according to reaction scheme B:

Scheme B

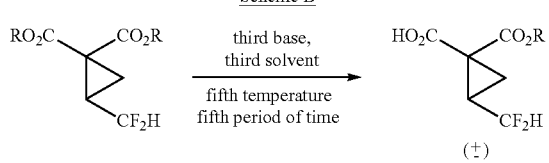

wherein R is alkyl.

In certain embodiments, the invention relates to a cyclopropanation method comprising:

heating a compound of formula C and trimethylsulfoxonium iodide in the presence of a second base and a second solvent at a fourth temperature for a fourth period of time, thereby forming a third product mixture comprising a compound of formula D,
wherein
formula C is

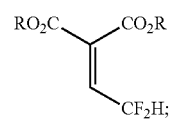

formula D is

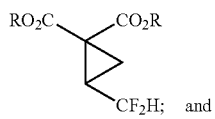

R is alkyl.

In certain embodiments, the compound of formula C is in admixture with

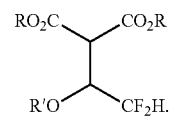

In certain embodiments, the invention relates to a condensation method comprising:

combining a compound of formula A with a compound of formula B at a first temperature for a first period of time in the presence of a first metal, a first solvent, and optionally a first base, thereby forming a first product mixture comprising a compound of formula C,
wherein
formula A is

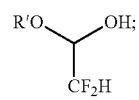

formula B is

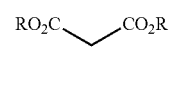

formula C is

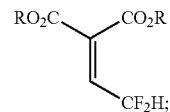

R is alkyl; and
and R' is alkyl.

In certain embodiments, the first product mixture further comprises

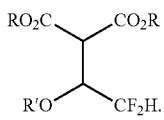

DETAILED DESCRIPTION OF THE INVENTION

I. Overview

In certain embodiments, the invention relates to a method of synthesizing compound 54, a difluoroamino acid, that is based on a Knoevenagel condensation, cyclopropanation, and resolution sequence. In certain embodiments, the resolution is accomplished by simulated moving bed chromatography. In certain embodiments, the resolution is an enzymatic resolution. In certain embodiments, the inventive synthesis of compound 54 eliminates the need for corrosive fluorination chemistry.

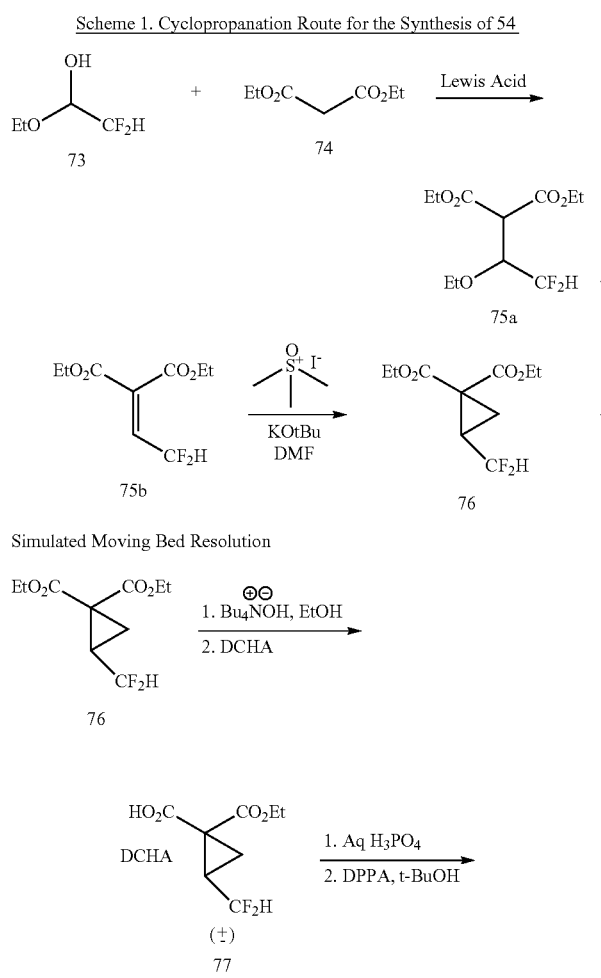

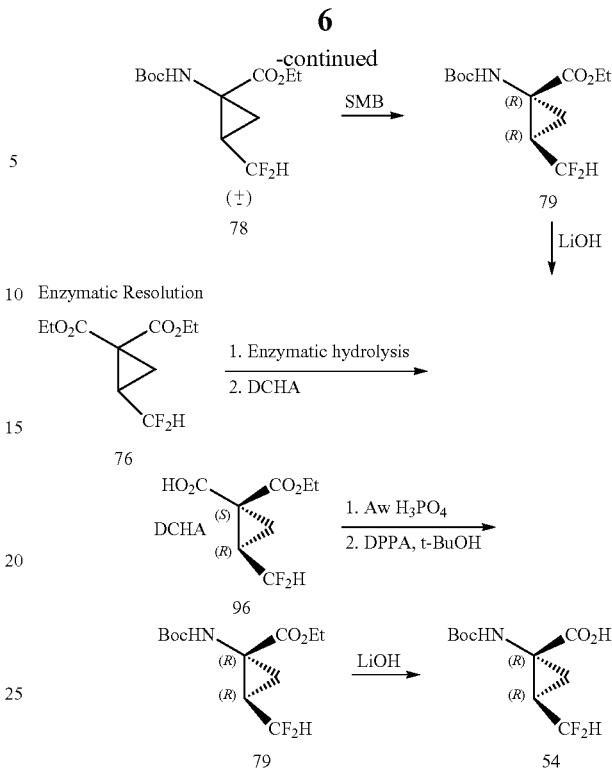

In certain embodiments, the invention relates to the synthesis of cyclopropyl diester 76. In certain embodiments, 76 is synthesized via a two-step Knoevenagel condensation/cyclopropanation sequence.

In certain embodiments, the invention relates to a method of synthesizing 79. In certain embodiments, 79 is synthesized by selective enzymatic hydrolysis. In certain embodiments, 79 is resolved from a racemic mixture (78) by simulated moving bed (SMB) chromatography or the like.

II. Definitions

Listed below are definitions of various terms used to describe this invention. These definitions apply to the terms as they are used throughout this specification and claims, unless otherwise limited in specific instances, either individually or as part of a larger group. The number of carbon atoms in a hydrocarbyl substituent can be indicated by the prefix "$C_x$-$C_y$," where x is the minimum and y is the maximum number of carbon atoms in the substituent.

The term "alkyl" as used herein, refers to a saturated, straight- or branched-chain hydrocarbon radical typically containing from 1 to 20 carbon atoms. For example, "$C_1$-$C_6$ alkyl" or "$C_1$-$C_8$ alkyl" contains from one to six, or from one to eight, carbon atoms, respectively. Examples of alkyl radicals include, but are not limited to, methyl, ethyl, propyl, isopropyl, n-butyl, tert-butyl, neopentyl, n-hexyl, heptyl, octyl radicals and the like.

The term "cycloalkyl" denotes a monovalent group derived from a monocyclic or polycyclic saturated carbocyclic ring compound. Examples of cycloalkyl include, but are not limited to, cyclopropyl, cyclobutyl, cyclopentyl, cyclohexyl, bicyclo[2.2.1]heptyl, and bicyclo[2.2.2]octyl and the like.

The term "amino-protecting group," as used herein, refers to a labile chemical moiety that can protect an amino group against undesired reactions during synthetic procedures.

After said synthetic procedure(s) the amino-protecting group as described herein may be selectively removed. Suitable amino-protecting groups are described generally in T. H. Greene and P. G. M. Wuts, Protective Groups in Organic Synthesis, 3rd edition, John Wiley & Sons, New York (1999). Examples of amino-protecting groups include, but are not limited to, t-butoxycarbonyl, 9-fluorenyl-methoxycarbonyl, benzyloxycarbonyl, and the like.

The term "protected amino," as used herein, refers to an amino group protected with an amino-protecting group as defined above.

As used herein, the term "salt" includes "pharmaceutically acceptable salts," which are, within the scope of sound medical judgment, suitable for use in contact with the tissues of humans and other vertebrates, preferably mammals, without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1-19 (1977). Such salts can be prepared in situ during isolation and purification of reaction products as described herein, or separately, such as by reacting a free base function with a suitable acid, such as an organic acid. Examples of pharmaceutically acceptable salts include, but are not limited to, hydrochloride, hydrobromide, phosphate, sulfate, perchlorate, acetate, maleate, tartrate, citrate, succinate, or malonate. Other pharmaceutically acceptable salts include, but are not limited to, adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, sulfate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, ammonium, quaternary ammonium, and amine cations associated with counterions such as halide, hydroxide, carboxylate, sulfate, phosphate, nitrate, alkyl having from 1 to 6 carbon atoms, sulfonate and aryl sulfonate. Particularly preferred salts for organic compounds having carboxylic acid functionality include metal salts and quaternary amine salts.

As used herein, the term "enantioenriched" means a mixture of enantiomers in which one of the two enantiomers is present in a larger amount. This term also encompasses an enantiomerically pure compounds (i.e., a compound having an enantiomeric excess (ee) greater than about 90%, greater than about 95%, preferably greater than about 98%, most preferably greater than 99%).

Various aspects of the invention are described in further detail herein.

III. Exemplary Compounds

In certain embodiments, the invention relates to a compound, or a salt thereof, having a structure selected from:

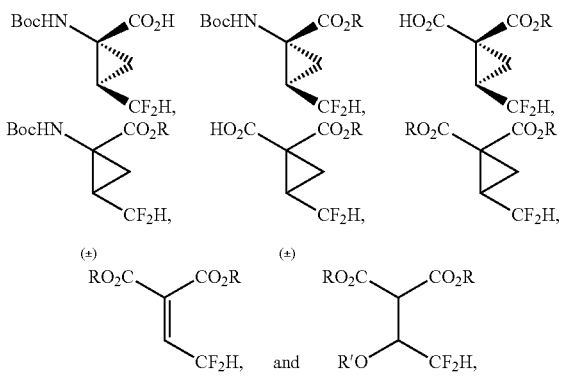

wherein, independently for each occurrence,

R is alkyl; and

R' is alkyl.

In certain embodiments, the invention relates to any one of the compounds described herein, wherein R is lower alkyl.

In certain embodiments, the invention relates to any one of the compounds described herein, wherein R is ethyl.

In certain embodiments, the invention relates to any one of the compounds described herein, wherein R is propyl.

In certain embodiments, the invention relates to any one of the compounds described herein, wherein R is isopropyl.

In certain embodiments, the invention relates to

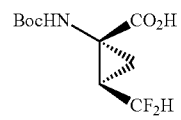

or a salt thereof.

In certain embodiments, the invention relates to

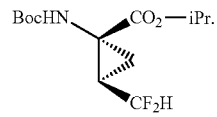

In certain embodiments, the invention relates to

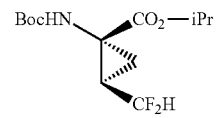

in crystalline form.

In certain embodiments, the invention relates to

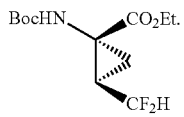

In certain embodiments, the invention relates to

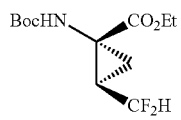

in crystalline form.

In certain embodiments, the invention relates to

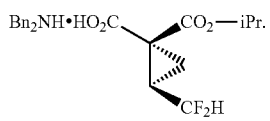

In certain embodiments, the invention relates to

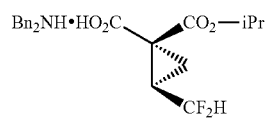

in crystalline form.

In certain embodiments, the invention relates to

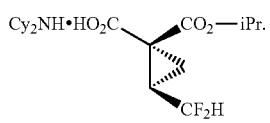

In certain embodiments, the invention relates to

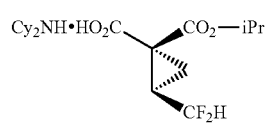

in crystalline form.

In certain embodiments, the invention relates to

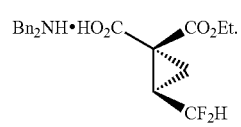

In certain embodiments, the invention relates to

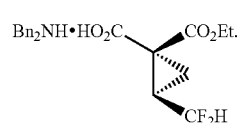

in crystalline form.

In certain embodiments, the invention relates to

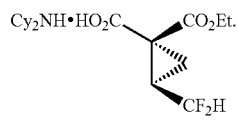

In certain embodiments, the invention relates to

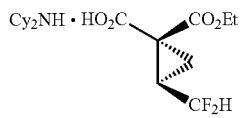

in crystalline form.

In certain embodiments, the invention relates to

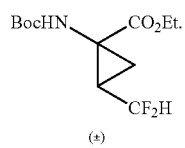

(±)

In certain embodiments, the invention relates to

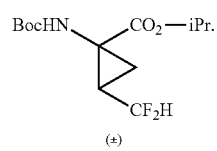

(±)

In certain embodiments, the invention relates to

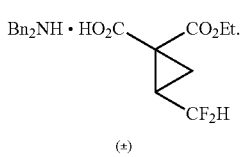

(±)

In certain embodiments, the invention relates to

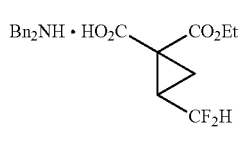

(±)

in crystalline form.

In certain embodiments, the invention relates to

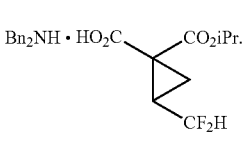

(±)

In certain embodiments, the invention relates to

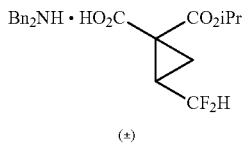
(±)

in crystalline form.

In certain embodiments, the invention relates to

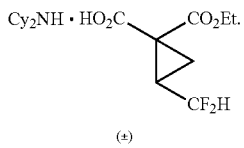
(±)

In certain embodiments, the invention relates to

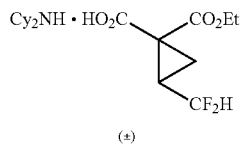
(±)

in crystalline form.

In certain embodiments, the invention relates to

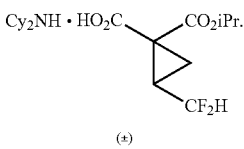
(±)

In certain embodiments, the invention relates to

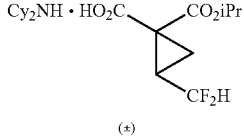
(±)

in crystalline form.

In certain embodiments, the invention relates to

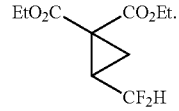

In certain embodiments, the invention relates to

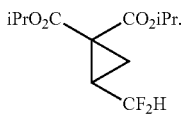

In certain embodiments, the invention relates to

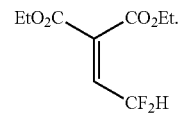

In certain embodiments, the invention relates to

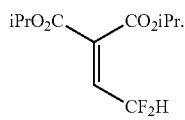

In certain embodiments, the invention relates to

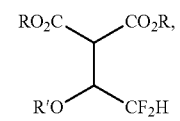

wherein R' is ethyl.

In certain embodiments, the invention relates to

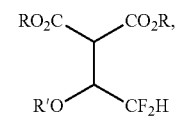

wherein R' is propyl.

In certain embodiments, the invention relates to

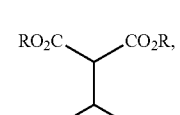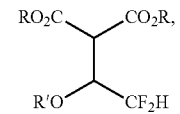

wherein R' is isopropyl.

In certain embodiments, the invention relates to

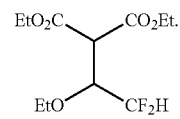

In certain embodiments, the invention relates to

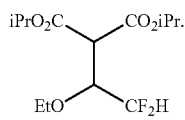

IV. Exemplary Methods and Uses

The compounds and processes of the present invention will be better understood in connection with the following illustrative methods by which the compounds of the invention may be prepared. It will be understood that any reaction described herein, in any of its variations, can be combined in sequence with one or more of the other reactions described herein, in any of their variations, substantially in analogy with the sequence shown in Scheme 1.

In certain embodiments, the invention relates to a hydrolysis method comprising:

contacting, in an eighth solvent, a compound of formula I with a fifth base, thereby forming a compound of formula J;

wherein
formula I is

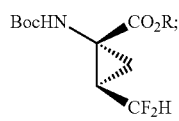

formula J is

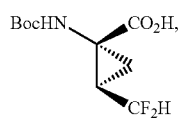

or a salt thereof; and
R is alkyl.

In certain embodiments, the invention relates to any one of the methods described herein, wherein the fifth base comprises KOH, NaOH, or LiOH, preferably NaOH or LiOH.

In certain embodiments, the invention relates to any one of the methods described herein, wherein the eighth solvent comprises EtOH, n-PrOH, i-PrOH, ethyl acetate, dioxane, DMF, acetonitrile, water or DMSO, preferably water or acetonitrile, or a mixture of water and EtOH, n-PrOH, or i-PrOH.

In certain embodiments, the invention relates to an enantioenrichment method comprising:

subjecting a compound of formula F to simulated moving bed chromatography, thereby obtaining the enantioenriched compound of formula I;

wherein
formula F is

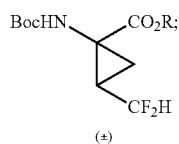

formula I is

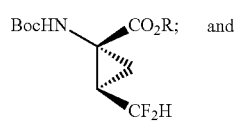

R is alkyl.

In certain embodiments, the invention relates to a method according to reaction scheme A:

Scheme A

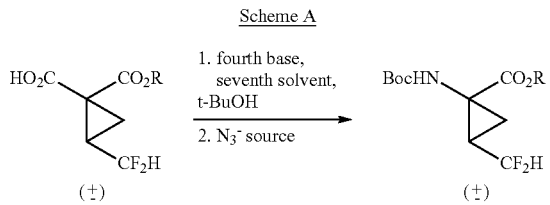

wherein R is alkyl.

In certain embodiments, the invention relates to a method according to reaction scheme A':

Scheme A'

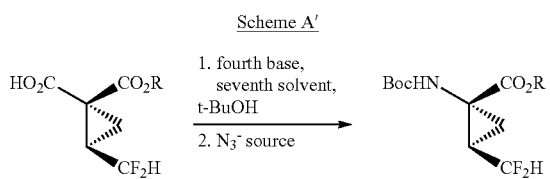

wherein R is alkyl.

In certain embodiments, the invention relates to any one of the methods described herein, wherein the fourth base comprises i-Pr$_3$N, (i-Pr)$_2$EtN, or triethylamine, preferably triethylamine.

In certain embodiments, the invention relates to any one of the methods described herein, wherein the fourth base comprises i-Pr$_3$N, (i-Pr)$_2$EtN, triethylamine, EtNH$_2$, Et$_2$NH, or (iPr)$_2$NH, preferably a tertiary amine, such as triethylamine.

In certain embodiments, the invention relates to any one of the methods described herein, wherein the seventh solvent comprises heptane, toluene, methyl tert-butyl ether, or dioxane, preferably heptane.

In certain embodiments, the invention relates to any one of the methods described herein, wherein the N$_3^-$ source is a diarylphosphorylazide (such as diphenylphosphorylazide) or tosylazide, preferably diphenylphosphorylazide.

In certain embodiments, the invention relates to any one of the methods described herein, further comprising crystallizing the reaction product of reaction scheme A or reaction scheme A' to obtain the compound in a crystalline form.

In certain embodiments, the invention relates to a sequential selective hydrolysis method comprising:

selectively hydrolyzing with a first enzyme the 2S-enantiomer of a compound of formula D, thereby forming a fourteenth product mixture;

separating from the fourteenth product mixture an enantioenriched amount of the 2R-enantiomer of a compound of formula D, thereby forming a fifteenth product mixture comprising an enantioenriched compound of formula G;

regioselectively hydrolyzing with a second enzyme the compound of formula G, thereby forming a sixteenth product mixture comprising a compound of formula H, wherein
formula D is $$\text{RO}_2\text{C} \diagdown\!\!\!\!\triangle\!\!\!\!\diagup \text{CO}_2\text{R};$$
$$\qquad\qquad \text{CF}_2\text{H}$$

formula G is $$\text{RO}_2\text{C} \diagdown\!\!\!\!\triangle\!\!\!\!\diagup \text{CO}_2\text{R};$$
$$\qquad\qquad \text{CF}_2\text{H}$$

formula H is $$\text{HO}_2\text{C} \diagdown\!\!\!\!\triangle\!\!\!\!\diagup \text{CO}_2\text{R},$$
$$\qquad\qquad \text{CF}_2\text{H}$$

or a salt thereof; and

R is alkyl.

In certain embodiments, the invention relates to any one of the methods described herein, wherein the selective hydrolysis the 2S-enantiomer of a compound of formula D takes place in a first buffer.

In certain embodiments, the invention relates to any one of the methods described herein, wherein the first buffer comprises sodium phosphate.

In certain embodiments, the invention relates to any one of the methods described herein, wherein the first buffer comprises sodium phosphate at a concentration from about 0.25 M to about 0.75 M. In certain embodiments, the invention relates to any one of the methods described herein, wherein the first buffer comprises sodium phosphate at a concentration of about 0.3 M, about 0.4 M, about 0.5 M, about 0.6 M, or about 0.7 M.

In certain embodiments, the invention relates to any one of the methods described herein, wherein the first buffer comprises sodium phosphate at about pH 7.

In certain embodiments, the invention relates to any one of the methods described herein, wherein the first enzyme is RML enzyme.

In certain embodiments, the invention relates to any one of the methods described herein, wherein the second enzyme is yvaK esterase.

In certain embodiments, the invention relates to any one of the methods described herein, further comprising isolating the compound of formula H from the sixteenth product mixture, thereby obtaining substantially pure compound of formula H.

In certain embodiments, the invention relates to a method according to reaction scheme B:

Scheme B $$\text{RO}_2\text{C} \diagdown\!\!\!\!\triangle\!\!\!\!\diagup \text{CO}_2\text{R} \xrightarrow[\text{fifth temperature}]{\text{third base, third solvent}} \text{HO}_2\text{C} \diagdown\!\!\!\!\triangle\!\!\!\!\diagup \text{CO}_2\text{R}$$

wherein R is alkyl.

In certain embodiments, the invention relates to any one of the methods described herein, wherein the third base comprises BnMe$_3$NOH (Triton B), CsOH, ammonium hydroxide, tetraalkylammonium hydroxide (such as tetrabutylammonium hydroxide), KOH, NaOH, or LiOH, preferably KOH or tetrabutylammonium hydroxide.

In certain embodiments, the invention relates to any one of the methods described herein, wherein the third solvent comprises t-BuOH, n-BuOH, n-PrOH, i-PrOH, EtOH, MeOH, or water, preferably i-PrOH, n-PrOH, EtOH, or water.

In certain embodiments, the invention relates to any one of the methods described herein, wherein the fifth temperature is from about 15° C. to about 40° C., for example, about 15° C., about 20° C., about 23° C., about 25° C., about 30° C., about 35° C., or about 40° C., preferably about 23° C.

In certain embodiments, the invention relates to any one of the methods described herein, wherein the fifth period of time is from about 1 h to about 18 h, for example, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, or about 18 h.

In certain embodiments, the invention relates to any one of the methods described herein, further comprising the step of crystallizing the reaction product of reaction scheme B to obtain the compound in a crystalline form.

In certain embodiments, the invention relates to any one of the methods described herein, further comprising the step of contacting the reaction product of reaction scheme B with a base to obtain a salt of the compound. In certain embodiments, the invention relates to any one of the methods described herein, further comprising the step of contacting the reaction product of reaction scheme B with a base to obtain a salt of the compound in a crystalline form.

In certain embodiments, the invention relates to any one of the methods described herein, wherein the reaction product of reaction scheme B is $$\text{Bn}_2\text{NH} \cdot \text{HO}_2\text{C} \diagdown\!\!\!\!\triangle\!\!\!\!\diagup \text{CO}_2\text{Et.}$$
$$\qquad\qquad\qquad \text{CF}_2\text{H}$$

In certain embodiments, the invention relates to any one of the methods described herein, wherein the reaction product of reaction scheme B is $$\text{Bn}_2\text{NH} \cdot \text{HO}_2\text{C} \diagdown\!\!\!\!\triangle\!\!\!\!\diagup \text{CO}_2i\text{Pr.}$$
$$\qquad\qquad\qquad \text{CF}_2\text{H}$$

In certain embodiments, the invention relates to any one of the methods described herein, wherein the reaction product of reaction scheme B is

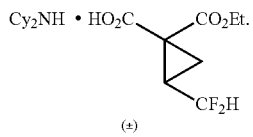
(±)

In certain embodiments, the invention relates to any one of the methods described herein, wherein the reaction product of reaction scheme B is

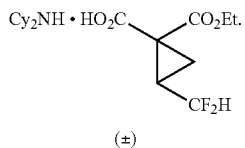
(±)

In certain embodiments, the invention relates to a cyclopropanation method comprising:

heating a compound of formula C and trimethylsulfoxonium iodide in the presence of a second base and a second solvent at a fourth temperature for a fourth period of time, thereby forming a third product mixture comprising a compound of formula D,
wherein
formula C is

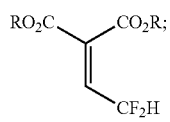

formula D is

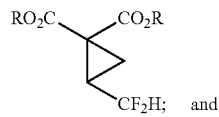  and

R is alkyl.

In certain embodiments, the invention relates to any one of the methods described herein, wherein the compound of formula C is present in a mixture with

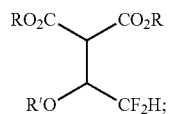

and R' is alkyl.

In certain embodiments, the invention relates to any one of the methods described herein, wherein the second base comprises NaH, LiH, NaHMDS, LiHMDS, KOt-Bu, or NaOt-Bu, preferably KOt-Bu.

In certain embodiments, the invention relates to any one of the methods described herein, wherein the second base comprises NaH, LiH, NaHMDS, LiHMDS, KOt-Bu, NaOt-Bu, (iPr)₂NH, triethylamine, preferably KOt-Bu.

In certain embodiments, the invention relates to any one of the methods described herein, wherein the second solvent comprises dimethylformamide (DMF), THF, methyl tert-butyl ether, ethyl acetate, dioxane, acetonitrile, or DMSO, preferably DMF.

In certain embodiments, the invention relates to any one of the methods described herein, wherein the fourth temperature is from about 35° C. to about 75° C., for example, about 35° C., about 40° C., about 45° C., about 50° C., about 55° C., about 60° C., about 65° C., about 70° C., or about 75° C., preferably about 55° C.

In certain embodiments, the invention relates to any one of the methods described herein, wherein the fourth period of time is from about 1 h to about 8 h, for example, about 1 h, about 2 h, about 3 h, about 4 h, about 5 h, about 6 h, about 7 h, or about 8 h, preferably about 5 h.

In certain embodiments, the invention relates to any one of the methods described herein, further comprising isolating the compound of formula D from the third product mixture, thereby forming substantially pure compound of formula D.

In certain embodiments, the invention relates to any one of the methods described herein, wherein the compound is

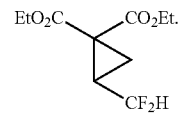

In certain embodiments, the invention relates to any one of the methods described herein, wherein the compound is

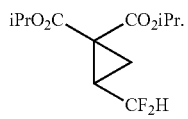

In certain embodiments, the invention relates to a condensation method comprising:

combining a compound of formula A with a compound of formula B at a first temperature for a first period of time in the presence of a first metal, a first solvent, and optionally a first base, thereby forming a first product mixture comprising a compound of formula C,
wherein
formula A is

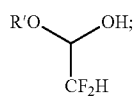

formula B is

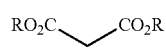

formula C is

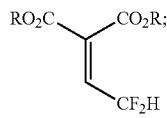

R is alkyl; and
and R' is alkyl.

In certain embodiments, the invention relates to any one of the methods described herein, wherein the first product mixture further comprises

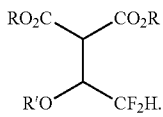

In certain embodiments, the invention relates to any one of the methods described herein, wherein the first metal comprises a titanium Lewis acid, such as a titanium alkoxide halide.

In certain embodiments, the invention relates to any one of the methods described herein, wherein the first metal comprises $TiCl_4$, $TiOR_4$, $CeCk_3$, $Ce_2(SO_4)_3$, $CaCl_2$, $MgCl_2$, $Ti(Oi-Pr)_3Cl$ or $Ti(OEt)_3Cl$.

In certain embodiments, the invention relates to any one of the methods described herein, wherein the first base is present; and the first base comprises $(i-Pr)_2EtN$, or triethylamine, preferably triethylamine.

In certain embodiments, the invention relates to any one of the methods described herein, wherein the first base is present; and the first base comprises $(i-Pr)_2EtN$, triethylamine, $EtNH_2$, $Et_2NH$, or $(iPr)_2NH$, preferably a tertiary amine, such as triethylamine.

In certain embodiments, the invention relates to any one of the methods described herein, wherein the first metal is $CeCl_3$ or $MgCl_2$; and the first base is absent.

In certain embodiments, the invention relates to any one of the methods described herein, wherein the first metal is $CeCl_3$ or $MgCl_2$; and the first metal is present in a catalytic quantity.

In certain embodiments, the invention relates to any one of the methods described herein, wherein the first metal is $TiCl_4$, $TiOR_4$, $Ti(Oi-Pr)_3Cl$, or $Ti(OEt)_3Cl$; and the first metal is present in a stoichiometric quantity.

In certain embodiments, the invention relates to any one of the methods described herein, wherein the first solvent comprises MeOH, EtOH, n-PrOH, i-PrOH, tetrahydrofuran (THF), methyl tert-butyl ether, ethyl acetate, dioxane, DMF, acetonitrile, or DMSO, preferably THF.

In certain embodiments, the invention relates to any one of the methods described herein, wherein the first metal is $TiCl_4$, $TiOR_4$, $Ti(Oi-Pr)_3Cl$, or $Ti(OEt)_3Cl$; and the first solvent comprises MeOH, EtOH, n-PrOH, i-PrOH, tetrahydrofuran (THF), methyl tert-butyl ether, ethyl acetate, dioxane, DMF, acetonitrile, or DMSO, preferably THF.

In certain embodiments, the invention relates to any one of the methods described herein, wherein the first metal is $CeCl_3$ or $MgCl_2$; and the first solvent comprises MeOH, EtOH, n-PrOH, i-PrOH, tetrahydrofuran (THF), methyl tert-butyl ether, ethyl acetate, dioxane, DMF, acetonitrile, or DMSO, preferably MeOH, EtOH, n-PrOH, or i-PrOH.

In certain embodiments, the invention relates to any one of the methods described herein, wherein the first temperature is from about $-10°$ C. to about $15°$ C., for example about $-10°$ C., about $-5°$ C., about $0°$ C., about $5°$ C., about $10°$ C., or about $15°$ C., preferably about $0°$ C.

In certain embodiments, the invention relates to any one of the methods described herein, wherein the first period of time is from about 6 h to about 18 h, for example, about 6 h, about 7 h, about 8 h, about 9 h, about 10 h, about 11 h, about 12 h, about 13 h, about 14 h, about 15 h, about 16 h, about 17 h, or about 18 h, preferably about 12 h.

In certain embodiments, the invention relates to any one of the methods described herein, further comprising heating the first product mixture at a second temperature.

In certain embodiments, the invention relates to any one of the methods described herein, wherein the second temperature is from about $16°$ C. to about $30°$ C., for example, about $20°$ C., about $23°$ C., about $25°$ C., or about $30°$ C., preferably about $23°$ C.

In certain embodiments, the invention relates to any one of the methods described herein, wherein the first product mixture is maintained at the second temperature for a second period of time.

In certain embodiments, the invention relates to any one of the methods described herein, wherein the second period of time is from about 1 h to about 3 h, for example, about 1 h, about 1.5 h, about 2 h, about 2.5 h, or about 3 h, preferably about 1.5 h.

In certain embodiments, the invention relates to any one of the methods described herein, further comprising heating the first product mixture at a third temperature.

In certain embodiments, the invention relates to any one of the methods described herein, wherein the third temperature is from about $35°$ C. to about $75°$ C., for example, about $35°$ C., about $40°$ C., about $45°$ C., about $50°$ C., about $55°$ C., about $60°$ C., about $65°$ C., about $70°$ C., or about $75°$ C., preferably about $55°$ C.

In certain embodiments, the invention relates to any one of the methods described herein, wherein the first product mixture is maintained at the third temperature for a third period of time.

In certain embodiments, the invention relates to any one of the methods described herein, wherein the third period of time is from about 1 h to about 3 h, for example, about 1 h, about 1.5 h, about 2 h, about 2.5 h, or about 3 h, preferably about 1.5 h.

In certain embodiments, the invention relates to any one of the methods described herein, further comprising isolating the compound of formula C from the first product mixture, thereby forming substantially pure compound of formula C.

In certain embodiments, the invention relates to any one of the methods described herein, wherein R is ethyl.

In certain embodiments, the invention relates to any one of the methods described herein, wherein R is propyl.

In certain embodiments, the invention relates to any one of the methods described herein, wherein R is isopropyl.

In certain embodiments, the invention relates to any one of the methods described herein, wherein the compound of formula C is

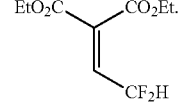

In certain embodiments, the invention relates to any one of the methods described herein, wherein the compound of formula C is

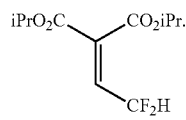

In certain embodiments, the invention relates to any one of the methods described herein, further comprising the steps outlined in any other method described herein.

In certain embodiments, the invention relates to the use of any one of the compounds described herein in the manufacture of a medicament.

Definitions of variables in the structures in the schemes herein are commensurate with those of corresponding positions in the formulae delineated herein.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers. Racemates, and Resolutions (John Wiley & Sons, 1981).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991): L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

EXEMPLIFICATION

The present invention is further illustrated by the following Example which should not be construed as limiting in any way. The Examples and discoveries described herein are representative. As such, the studies and results described in the Examples section herein may be used as a guideline.

Example 1—Synthesis of 54 Via Cyclopropanation

Overview

The cyclopropanation route for the synthesis of compound 54 is outlined in Scheme 1. The synthesis starts with the Knoevenagel condensation of diethylmalonate 74 with hemi-acetal 73 followed by cyclopropanation to give diester 76. The Knoevenagel condensation of malonate esters with the aldehyde hemiacetal 73 can be conducted with Lewis acids such as $TiCl_4$, $Ti(OEt)_4$, $TiCl(OEt)_3$, $CeCl_3$, $Ce_2(SO_4)_3$, $MgCl_2$, $CaCl_2$ and the like. Two methods were developed for the conversion of the racemic diester 76 into the enantiomerically pure acid 54. The first method involves simulated moving bed chromatographic resolution of the racemic ester 78 to give the resolved (R,R) ester 79. The second method utilizes enzymatic resolution of 76 to prepare the resolved (R,R) acid 96. Both methods converge at the last step in the saponification of the resolved ester 79 to the acid 54.

Knoevenagel Condensation with Catalytic $CeCl_3$/NaI

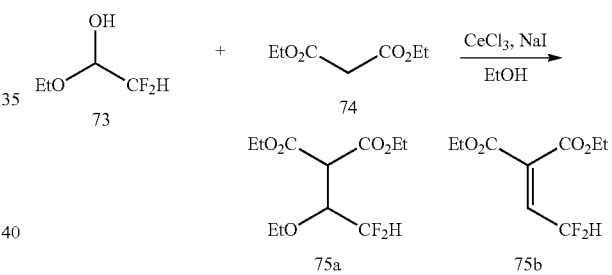

To a flask was charged $CeCl_3$ (1.54 g, 6.25 mmol, 0.05 equiv), NaI (0.94 g, 6.25 mmol, 0.05 equiv) and ethanol (80 mL) and the mixture was stirred with heating to 65° C. At reaction temperature of 65° C. a pre-mixed solution of diethyl malonate (20 g, 125 mmol) and 21.0 g difluoroacetaldehyde ethyl hemiacetal (90% w/w, 150 mmol, 1.2 equiv) was charged. The resulting mixture was stirred at 60-65° C. Upon completion the reaction was cooled to ambient temperature and inorganic solids were filtered off. The filtrate was concentrated under vacuum to near completion, diluted with dimethylformamide (DMF) (74 g), and concentrated under vacuum to remove the residual ethanol. The DMF solution is used directly in the next step as both 75a and 75b are converted to product in the cyclopropanation step.

Knoevenagel Condensation with Catalytic $MgCl_2$

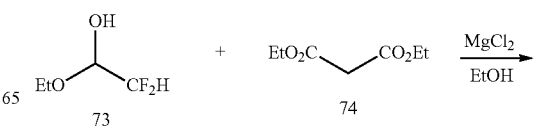

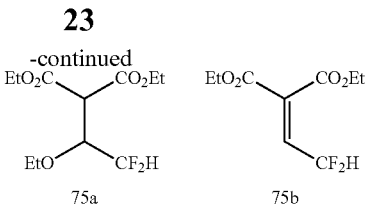

To a flask was charged MgCl$_2$ (1.189 g, 12.49) and EtOH (140 mL, 200 proof) and to this solution at ambient temperature, difluoroacetaldehyde ethyl hemiacetal (38.5 g, 90% w/w, 275 mmol, 1.1 equiv) was charged, followed by addition of diethyl malonate (40.0 g, 250 mmol). The resulting mixture was stirred at 60-65° C. Upon completion the reaction mixture was cooled to ambient temperature and concentrated under vacuum to remove most of the ethanol. The mixture was filtered to remove inorganic salts, DMF (74 g) was added to the filtrate, and concentrated under vacuum to remove the residual ethanol. The DMF solution is used directly in the next step.

Alternatively the reaction mixture can be worked up by concentration under vacuum to remove most of the ethanol, addition of methyl tert-butyl ether (MTBE) (300 mL) and washing with 150 mL 1 M HCl and then 150 mL brine. The MTBE solution is dried with MgSO$_4$, filtered, concentrated under vacuum, diluted with DMF, and concentrated under vacuum to remove the residual MTBE. The DMF solution is used directly in the next step.

Other Lewis acids catalysts which have been tested include CaCl$_2$ and Ce$_2$(SO$_4$)$_3$.

Knoevenagel Condensation with TiCl(OEt)$_3$

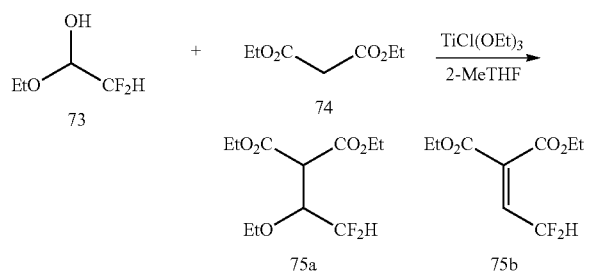

Titanium (IV) ethoxide (3.6 kg, 15.7 mol) and 2-MeTHF (18.5 kg) were charged to a flask. Acetyl chloride (1.2 kg, 15.7 mol) was added, rinsing with 2-MeTHF (2.0 kg). The mixture heated to reflux for 2 h and then cooled to 20° C. and held overnight. The mixture was cooled to −3° C. and diethyl malonate (1.2 kg, 7.5 mol) was added, rinsing with 2-MeTHF (1.7 kg). The difluoroacetaldehyde ethyl hemiacetal (1.0 kg, 7.5 mol) was added, rinsing with 2-MeTHF (1.7 kg). Then triethylamine (1.6 kg, 15.7 mol) was added and the mixture stirred at 0° C. for 4 h. The mixture was gradually heated to 50-57° C. and mixed for 2 h and then cooled to 20° C. and held overnight. The mixture was cooled to 3° C. and quenched with 1 M HCl (10.9 kg), mixed at 15° C., and the layers separated. The organic layer was wash with 1 M HCl (6.2 kg) and then 20% brine (6.8 kg). The product solution was dried with MgSO$_4$, filtered, rinsing with 2-MeTHF. The filtrate was concentrated under vacuum to near completion, DMF (4.7 L) was added, and the concentration continued to remove the 2-MeTHF. The DMF solution is used directly in the next reaction.

Cyclopropanation

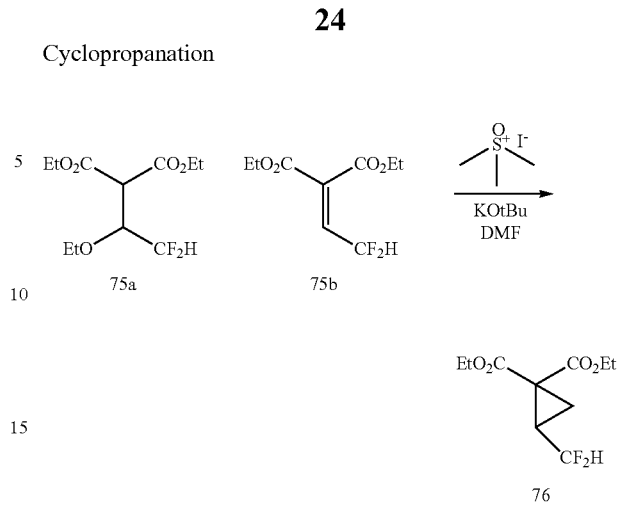

To a flask was charged potassium tert-butoxide (1.0 kg, 9.0 mol, 1.2 equiv), trimethylsulfoxonium iodide (2.0 kg, 9.0 mol, 1.2 equiv), and DMF (7.0 L). The mixture was stirred for 2 h, and then a solution of 75a and 75b (7.5 mol theoretical) mixture in DMF was added. The reaction was heated to 55° C. for 3.5 h and then cooled to 5° C. and mixed overnight. The reaction was quenched with a cold mixture of MTBE (14.4 L) and water (14.4 L), then mixed and warmed and the layers separated. The aqueous layer was re-extracted with MTBE (14.4 L) and the combined organic layers were washed with 20% brine (2×6.8 kg), and then with water (2×6 kg). The product solution was concentrated and solvent switched to EtOH and assayed for 80% yield of 76.

Chemical Hydrolysis

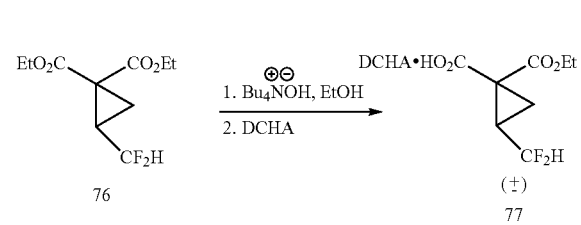

Tetrabutylammonium hydroxide (40 wt % aqueous, 4.3 kg) was added to the EtOH solution of compound 76 (7.5 mol theoretical from 74) and mixed at 20° C. Upon reaction completion, MTBE (14.4 L) was added and the mixture was cooled and 0.5 M HCl (14.4 L) was added. The mixture was warmed to 20° C.; the aqueous layer was separated and re-extracted with MTBE (6 L). The combined organic layers were washed with 20% brine solution (6.8 kg), and then water (6 L). The product was crystallized as the dicyclohexylamine salt from MTBE/heptanes. After filtration and drying a total of 1124 g of compound 77 was isolated (38% yield from 74).

Curtius Rearrangement

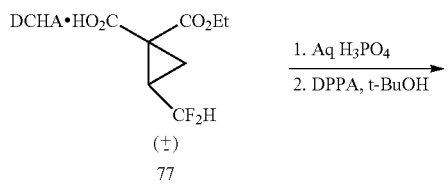

-continued

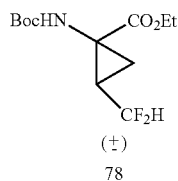

To a flask was charged compound 77 dicyclohexylammonium (DCHA) salt (1.1 kg) and MTBE (11 L) and the mixture was washed twice with 7% phosphoric acid (11 L, 5.2 L), once with 20% brine (3.1 kg), and once with water (2.8 L). The organic layer was diluted with heptane (5.5 L) and concentrated under vacuum to a volume of ~4 L. Then tert-butanol (1.1 kg) and heptane (4 L) were added followed by triethylamine (437 g). The mixture was heated to reflux (76° C.) and then diphenylphosphorylazide (757 g) was added over 1.5 h. After heating for 10 h, the mixture was cooled to 20° C. and concentrated under vacuum to a volume of ~4 L. The mixture was diluted with MTBE (5.8 L) and successively washed with 5% aqueous citric acid (5.8 L), 8% aqueous NaHCO$_3$ (3.2 kg), 20% brine (3.4 kg), and water (3 L). The product solution in MTBE was solvent switched to acetonitrile (CH$_3$CN or MeCN or ACN) and the final solution assayed for 542 g of 78 for a 68% yield.

Simulated Moving Bed Resolution

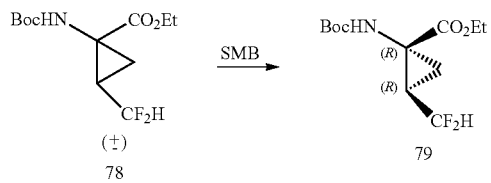

Racemic Boc amino acid ethyl ester 78 was subjected to simulated moving bed chromatography (SMB) to yield the (1R,2R) enantiomer 79.

Saponification

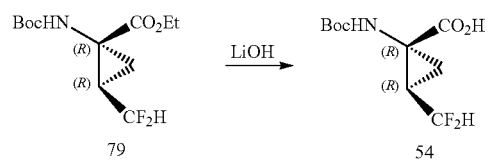

A solution of the Boc amino ethyl ester 79 (2 g, 7.16 mmol) in acetonitrile (10 mL) was treated with a solution of LiOH (193 mg, 7.88 mmol 1.1 equiv) in water (10 mL). The mixture was stirred at ambient temperature overnight. Upon reaction completion, 15% aqueous citric acid was added to achieve a pH of 4-4.5. The mixture was concentrated under vacuum to remove the acetonitrile and the resulting mixture was diluted with 5 mL water. The resulting slurry was mixed overnight at ambient temperature, filtered and washed with 4 mL water. The wet cake was dried in a vacuum oven to give an isolated yield of 80%.

Enzymatic Resolution

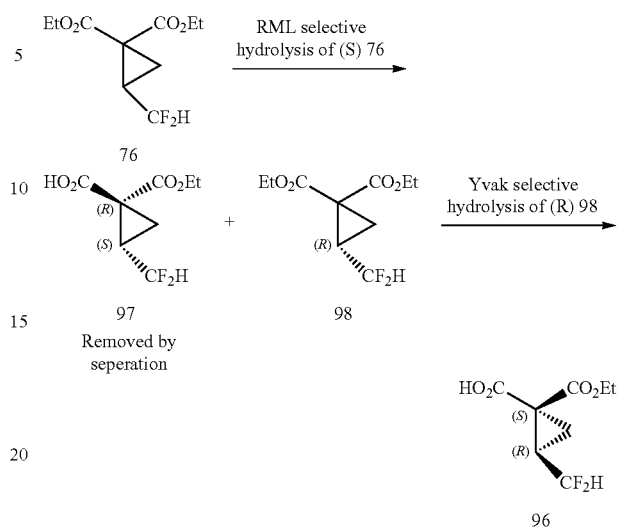

The racemic diester 76 (1 g) was dissolved in 300 mL of 0.5 M sodium phosphate buffer, pH 7.0. To the reaction was added 15.3 mL of 3× dialyzed RML enzyme. The reaction was incubated at 30° C. and 125 revolutions per minute (rpm) for 96 hrs. Upon reaction completion, the desired unreacted (R) diester 98 was recovered from the aqueous reaction phase by extraction into MTBE (2×60 mL). The (S) acid 97 remained in the aqueous layer. The combined MTBE extracts were dried using magnesium sulfate, concentrated in vacuo and the recovered diester 98 was then dissolved in 0.5 M 150 mL sodium phosphate, pH 7.0 for use in the second resolution step.

YvaK clarified cell lysate (10 mL) was added to the solution of diester 98 in the sodium phosphate buffer. The reaction was incubated at 30° C. and 125 rpm for 96 hrs. Upon reaction completion, the pH was adjusted to 3 by addition of 5 N HCl. The acid product 96 was recovered from reaction aqueous phase by repeated extraction with MTBE (3×60 mL). The combined MTBE extracts were dried using magnesium sulfate and evaporated in vacuo to remove MTBE. The final recovered product (1S,2R) acid 96 in MTBE was filtered through Celite.

The acid 96 can be converted into the DCHA salt as described for compound 77. The acid 96, or its DCHA salt, can be converted into acid 54 by following the procedures described for the Curtius rearrangement (converting 77 to 78) and saponification (converting 79 to 54).

RML Dialysis Procedure: *Mucor miehei* lipase (RML, 6 mL) was placed in ~10 inches of 6-8 kDa molecular weight cut-off (MWCO) dialysis membrane and dialyzed for 4 hours in 2 liters of 0.1M sodium phosphate buffer, pH 7.0 at 4° C. and approx. 125 rpm. After 4 hours, the buffer was exchanged for 2 L of fresh 0.1M sodium phosphate buffer, pH 7.0 for an additional 24 hours. After 24 hours, the buffer was exchanged a third time for 2 L of fresh 0.1 M sodium phosphate buffer, pH 7.0 for an additional 24 hours. The final dialysis product results in ~18 mL of 3× dialyzed RML.

YvaK Clarified Cell Lysate-Enzyme Preparation Procedure: *Bacillus subtilis* esterase 'yvaK' (Gene ID-BSU33620) was inserted into pET21b vector at MCS between NdeI and BamHI restriction sites and transformed into BL21(DE3) competent cells. The yvaK esterase was subsequently expressed by growing the culture at 30° C., 225 rpm until an OD$_{600}$ of 0.5-0.8. Protein expression was induced with isopropyl β-D-1-thiogalactopyranoside (IPTG) to 0.1 mM and incubated for another for 18 hours. The resulting cell culture was pelleted by centrifugation at 3750 rpm, 30 min, 4° C. and stored at −80° C. until use. Cell pellets were resuspended in 0.5 M sodium phosphate buffer, pH 7.0 at a ratio of 1:10 resuspension buffer volume to expression culture volume. Resuspended culture was sonicated on ice three times for 30 s and centrifuged at 3750 rpm, 30 min, 4° C. The resulting supernatant was used as the clarified cell lysate solution.

Example 2

Stage 1. Titanium-Mediated Knoevenagel

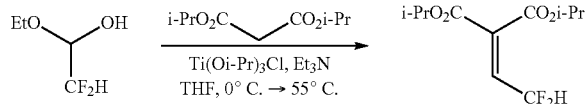

A 2-L three-necked round bottom flask, equipped with a mechanical stirrer, pressure equalizing addition funnel and reflux condenser, was charged with chlorotitanium triisopropoxide (74.4 g, 68.2 mL, 285 mmol) and 570 mL THF [Note: Chlorotitanium triisopropoxide is a solid at room temperature. We found that warming the bottle in a 55° C. bath for 30 min provided an oil that could be easily transferred via syringe]. The solution was cooled to 0° C. and held at this temperature for 20 min. The solution was then charged with diisopropyl malonate (26.9 g, 27.1 mL, 143 mmol) and difluoroacetaldehyde ethyl hemiacetal (20 g, 143 mmol, 90% purity) [Note: The purity was confirmed by $^1$H-NMR using 1,3-Bis(trifluoromethyl)-5-bromobenzene as an internal standard]. The addition funnel was charged with triethylamine (28.9 g, 40 mL, 285 mmol) and added dropwise over 20 min [Note: triethylamine hydrochloride begins precipitating upon addition]. Upon complete addition of triethylamine, the mixture was stirred at 0° C. for 12 h (complete consumption of diisopropyl malonate). The mixture was then warmed to ambient temperature and allowed to stir for 1.5 hours. After this time, the mixture was warmed to 55° C. (bath temp) and stirred for an additional 1.5 h [Note: $^1$H-NMR analysis showed nearly complete conversion to the alkylidene malonate and <5% of the intermediate alcohol. At this point ~15% of the fully transesterified (bis-ethyl ester) alkylidene malonate was present. This product can be reduced to ~5% by addition of titanium tetraisopropoxide (30.4 g, 31.7 mL, 107 mmol) and allowing the reaction to proceed at 55° C. for an additional 12 h.]. When the reaction was complete, it was cooled to 0° C. with an ice bath, diluted with 500 mL methyl tert-butyl ether (MTBE), and quenched by slow addition of 250 ml, 1 N HCl [Note: The mixture became very thick after the addition of 50 mL of 1 N HCl. Upon addition of another 50 mL, the thick suspension became an easily stirred suspension and after complete addition of HCl the solids were completely dissolved]. The biphasic mixture was poured into a 3-L reparatory funnel and the layers were cut. The bottom aqueous phase was extracted with an additional 500 mL MTBE [Note: The phase separation was much slower with the second extraction and took ~20 min for clean phase separation]. The bottom aqueous layer was again extracted with 500 mL MTBE, giving a very clean phase cut. The organics were combined and washed with 100 mL 1 N HCl. The phases cut and the organics washed with 500 mL sat. aq. NaCl. The organic phase was dried over MgSO$_4$, filtered, and concentrated under reduced pressure. The mass of the crude oil was 36.3 g (theory=35.7 g). This material was used without further purification.

Stage 2. Cyclopropanation with Corey's Salt

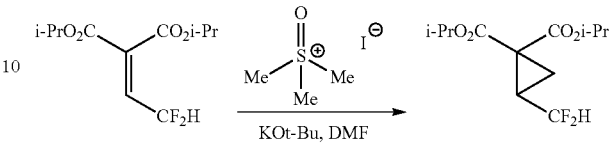

[Note: Reagent charges are based on 100% purity from the previous reaction]. A 500-mL three-necked round bottom flask, equipped with a mechanical stirrer and reflux condenser, was charged with potassium tert-butoxide (19.3 g, 172 mmol), trimethylsulphoxonium iodide (37.8 g, 172 mmol), and 140 mL dimethylformamide (DMF) [Note: Trimethylsulphoxonium iodide (Corey's salt) purchased from Aldrich was a pale yellow solid when received. Recrystallization of the salt from water (15 g/150 mL H$_2$O) followed by grinding of the solid to a powder and drying at 80° C. overnight provided white crystals]. After 20 min of stirring a clear solution was produced and was allowed to stir for an additional 1.5 h. To the solution of the glide was added a solution of the alkylidene malonate (35.8 g, 143 mmol) prepared above in 30 mL DMF [Note: An exotherm was noted upon addition and an easily stirred precipitate is formed]. The reaction vessel was placed in a preheated oil bath at 55° C. and stirred at this temperature for 2 h. After this time, the solution was cooled to room temperature (an ice bath can be used to aid in the cooling process) and 150 mL H$_2$O and 500 mL MTBE pre-cooled to 0° C. The biphasic mixture was stirred at 0° C. for 15 min and the mixture was poured into a 3-L reparatory funnel and the layers were cut. The bottom aqueous phase was extracted three times with 500 mL MTBE. The organic layers were combined and washed with H$_2$O (2×250 mL) and brine (2×250 mL). The organic phase was dried over MgSO$_4$, filtered, and concentrated in vacuo. The mass of the crude oil was 35 g (theory=37.8 g). This material was used without further purification.

Stage 3. Mono-Hydrolysis

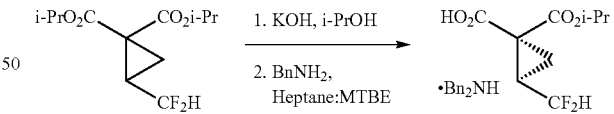

[Note: Reagent charges are based on 100% purity from the previous reaction]. A 500-mL three-necked round bottom flask, equipped with a mechanical stirrer and pressure equalizing addition funnel, was charged with the bis-isopropyl ester (32.1 g, 121 mmol) and isopropanol (150 mL). The addition funnel was charged with a solution of KOH (9.6 g, 145 mmol, 85%) in H$_2$O (30 mL). The KOH solution was added over 4 h. The mixture was allowed to stir for an additional 2 h at room temperature [Note: $^1$H-NMR analysis indicated ~94% conversion and a 4:1 mixture of mono-acid to di-acid]. The reaction mixture was cooled to 0° C. and held at this temperature for 20 min before the addition of 55 mL 2 N HCl (~pH 2). The majority of the organic layer was removed under reduced pressure and the remaining aqueous layer was poured into a separatory funnel with the aid of MTBE. The aqueous layer was extracted with MTBE (2×250 mL). The organics were then washed with 100 mL sat. aq. NaCl, dried over MgSO$_4$, filtered, and concentrated under reduced pressure.

The crude oil was dissolved in a heptane:MTBE mixture (4:1, 300 mL) and cooled to 0° C. Dibenzylamine (24 g, 23.4 mL, 121 mmol) was added to the cooled solution and the resulting slurry was stirred at 0° C. for 1 h [Note: A sonicating bath can be used if a gel is formed on the bottom of the flask. Sonicating the mixture for 20 min appears to break up the gel and produces an easily stirred suspension.] The solids were filtered and washed with 500 mL heptane to provide the crude dibenzylamine salt (48 g).

In order to remove the diacid by-product, the crude salt (containing both the mono-acid and di-acid salts, ~4:1) was placed in a 2-L round bottom flask with 500 mL MTBE. The mixture was heated at 60° C. for 30 min and cooled to room temperature [Note: the mono-acid salt is in solution and the di-acid salt remains as a solid]. The remaining solid was filtered from the mixture. [Note: The solid may be analyzed to ensure that the mono-acid salt has been completely solubilized. The above process can be repeated as necessary, adjusting the volume of MTBE used]. The MTBE was then removed under reduced pressure to provide an off white solid. Recrystallization of the mono-acid salt from isopropyl alcohol (IPA) (100 mL) and drying under reduced pressure provided the title compound (27.5 g, 54% overall yield) as a white solid.

Stage 4. Curtius Rearrangement

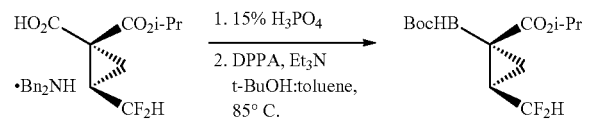

Salt Break:

A 1-L round bottom flask, equipped with a teflon coated magnetic stirbar, was charged with the above dibenzylamine salt (20.3 g, 10.75 mmol) and MTBE (200 mL). To this suspension was added a 15% H$_3$PO$_4$ solution (w/w, 200 mL) and the resulting mixture was stirred at room temperature for 45 min. The resulting solution was poured into a 1-L separatory funnel and the layers were cut. The top organic layer was washed with an additional 50 mL 15% H$_3$PO$_4$ and the layers cut. The organic layer was then washed with sat. aq. NaCl, the layers cut, and the organics dried over MgSO$_4$. After filtration of the MgSO$_4$, the solvent was removed in vacuo. The free acid was azeotropically dried with toluene (3×50 mL toluene) to remove water to under 100 ppm. The final toluene solution (~20 mL total volume) contained 96 ppm water (Karl Fischer).

Curtius Rearrangement:

A separate 1-L three-necked flask equipped with a mechanical stirrer and pressure equalizing addition funnel, was charged with t-BuOH (200 mL), triethylamine (9.8 g, 13.5 mL, 97 mmol), and the toluene solution of the carboxylic acid [Note: t-BuOH was stirred over 4-Å molecular sieves at 35° C. for 2 hours to remove water to under 100 ppm]. The mixture was then heated to 90° C. (bath temperature). The addition funnel was charged with a solution of DPPA (13.3 g, 10.4 mL, 48.4 mmol) in toluene (50 mL). The DPPA solution was added over a 5-hour period and the mixture was allowed to stir for an additional 6 hours after complete addition. The solvent removed under reduced pressure and the crude oil was dissolved in 500 mL MTBE and added to a 1-L separatory funnel. The organic phase was first washed 100 mL 5% citric acid and the layers cut. The organic phase was then washed with 100 ml, sat. aq. NaHCO$_3$ and the layers cut. The organics were then washed with 100 mL H$_2$O and the layers cut. Finally the organics were washed with 100 mL sat. aq. NaCl and the layers cut. The organic phase was dried over MgSO$_4$, filtered, and concentrated to provide a tan solid. The solid was crystallized from a minimal amount of heptane (~40 mL) to provide 10.3 g of a light-brown crystalline solid (~4% of the symmetrical urea by-product was contained in this material). [Note: The urea by-product can be removed by passing the mixture through a 25-g plug of silica gel eluting with 25% ethyl acetate (EtOAc) in hexanes. This provided 9.9 g of the product as a white crystalline solid.] After passing the mother liquor through a 10-g plug of silica gel and recrystallizing from heptane, an additional 1.6 g of the Boc-amino ester was obtained. The total mass of the product was 11.5 g corresponding to an 81% yield.

Example 3

Stage 1. Titanium-Mediated Knoevenagel

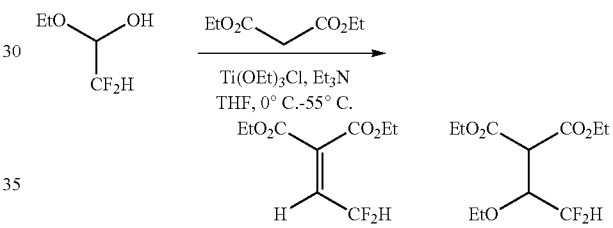

A 2-L three-necked round bottom flask, equipped with a mechanical stirrer, pressure equalizing addition funnel and reflux condenser, was charged with chlorotitanium triethoxide (15.3 g, 70 mmol) and 140 mL THF. The solution was cooled to 0° C. and held at this temperature for 20 min. The solution was then charged with diethyl malonate (5.61 g, 5.34 mL, 35 mmol) and difluoroacetaldehyde ethyl hemiacetal (4.9 g, 35 mmol, 90% purity) [Note: The purity was confirmed by $^1$H-NMR using 1,3-Bis(trifluoromethyl)-5-bromobenzene as an internal standard]. The addition funnel was charged with triethylamine (7.09 g, 9.8 mL, 70 mmol) and added dropwise over 20 min [Note: triethylamine hydrochloride begins precipitating upon addition]. Upon complete addition of triethylamine, the mixture is stirred at 0° C. for 12 h (complete consumption of diethyl malonate). The mixture is then warmed to ambient temperature and allowed to stir for 1.5 hours. After this time, the mixture is warmed to 55° C. (bath temp) and stirred for an additional 1.5 h. When the reaction was complete, it was cooled to 0° C. with an ice bath, diluted with 200 mL MTBE, and quenched by slow addition of 50 1 N HCl. The biphasic mixture was poured into a 1-L separatory funnel and the layers were cut. The bottom aqueous phase was extracted with an additional 100 mL MTBE. The bottom aqueous layer was again extracted with 100 mL MTBE, giving a very clean phase cut. The organics were combined and washed with 25 mL 1 N HCl. The phases cut and the organics washed with 50 mL sat. aq. NaCl. The organic phase was dried over MgSO$_4$, filtered, and concentrated under reduced pressure. The mass of the crude oil was 7.62 g (theory=7.78 g). This material was used without further purification.

Stage 2. Cyclopropanation with Corey's Salt

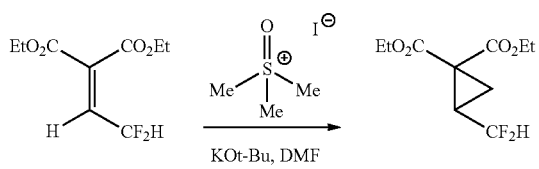 [SMILES: CCOC(=O)C(=CC(F)F)C(=O)OCC ; C[S+](C)(C)=O ; [I-] ; CCOC(=O)C1(C(=O)OCC)CC1C(F)F]

[Note: Reagent charges are based on 100% purity from the previous reaction]. A 25-mL round bottom flask, equipped with a teflon coated magnetic stirbar, was charged with potassium tert-butoxide (535 mg, 4.76 mmol, 97% purity), trimethylsulphoxonium iodide (1.05 g, 4.76 mmol), and 5 mL DMF [Note: Trimethylsulphoxonium iodide (Corey's salt) purchased from Aldrich was a pale yellow solid when received. Recrystallization of the salt from water (15 g/150 mL $H_2O$) followed by grinding of the solid to a powder and drying at 80° C. overnight provided white crystals]. After 15 min of stirring a clear solution was produced and was allowed to stir for an additional 1 h. To the solution of the ylide was added a solution of the alkylidene malonate (882 mg, 3.97 mmol) prepared above in 2.5 mL DMF [Note: the reaction is exothermic]. The reaction vessel was placed in a preheated oil bath at 55° C. and stirred at this temperature for 5 h. After this time, the solution was cooled to room temperature and poured into a mixture of 10 mL $H_2O$ and 25 mL MTBE precooled to 0° C. The biphasic mixture was stirred at 0° C. for 5 min then allowed to warm to room temperature. The mixture was poured into a 125-mL separatory funnel and the layers were cut. The bottom aqueous phase was extracted with an additional 25 mL MTBE. The organic layers were combined and washed with sat. aq. NaCl (15 mL). The organic phase was dried over $MgSO_4$, filtered, and concentrated in vacuo. The mass of the crude oil was 845 mg (theory=938 mg). The material was used without further purification.

Stage 3. Mono-Hydrolysis

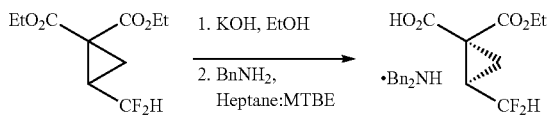

[Note: Reagent charges are based on 100% purity from the previous reaction]. A 100-mL round bottom flask, equipped with a magnetic stirbar, was charged with the diester (5.50 g, 23.3 mmol), ethanol (25 mL) and water (5 mL). To this mixture was added potassium hydroxide (1.27 g, 22.70 mmol) and the reaction stirred at room temperature. After 12 h, the mixture was cooled to 0° C. and acidified with 20 mL 1 N HCl (~pH 2). The solvent was removed in vacuo and the remaining aqueous layer poured into a 250-mL separatory funnel with the aid of MTBE. The aqueous layer was extracted with MTBE (200 mL). The organic phase was washed with 25 ml, sat. aq. NaCl, dried over $MgSO_4$, filtered, and concentrated under reduced pressure to give 4.5 g of a crude pale yellow oil.

The crude oil was dissolved in a heptane:MTBE mixture (4:1, 60 mL) and cooled to 0° C. Dibenzylamine (4.6 g, 4.5 mL, 23.3 mmol) was added to the cooled solution and the resulting slurry was stirred at 0° C. for 1 h. The solid was filtered and washed with heptane (100 mL) to provide 7.3 g of the crude dibenzylamine salt. To the crude solid was added MTBE (150 mL) and the mixture heated to reflux and held at this temperature for 10 min. At this point most of the solid had dissolved and the flask was then cooled to room temperature and the remaining solid (diacid.$Bn_2NH$) was collected by filtration. The MTBE solution of the mono-acid was evaporated and the remaining solid was recrystallized from 5:1 EtOH:$H_2O$ (25 mL) to provide 4.9 g (52% overall) of the title compound as a white solid.

Stage 4. Curtius Rearrangement (DPPA)

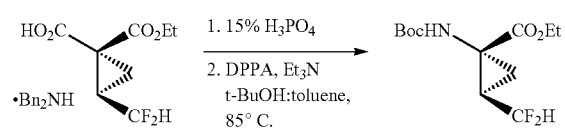 [SMILES: "·Bn2NH" ; CCOC(=O)[C@@]1(C(=O)O)C[C@H]1C(F)F ; CCOC(=O)[C@@]1(NC(=O)OC(C)(C)C)C[C@H]1C(F)F]

Salt Break:

A 250-mL round bottom flask, equipped with a teflon coated magnetic stirbar, was charged with the above dibenzylamine salt (5.6 g, 13.81 mmol) and MTBE (70 mL). To this suspension was added a 15% $H_3PO_4$ solution (w/w, 70 mL) and the resulting mixture was stirred at room temperature for 45 min. The resulting solution was poured into a 500-mL separatory funnel and the layers were cut. The top organic layer was washed with an additional 20 mL 15% $H_3PO_4$ and the layers cut. The organic layer was then washed with sat. aq. NaCl, the layers cut, and the organics dried over $MgSO_4$. After filtration of the $MgSO_4$, the solvent was removed in vacuo. The free acid was azeotropically dried with toluene (3×25 mL toluene) to remove water to under 100 ppm.

Curtius Rearrangement:

A separate 500-mL three-necked flask equipped with a mechanical stirrer and pressure equalizing addition funnel, was charged with t-BuOH (125 mL), triethylamine (2.79 g, 3.9 mL, 27.6 mmol), and the toluene solution of the carboxylic acid [Note: t-BuOH was stirred over 4-Å molecular sieves at 35° C. for 2 hours to remove water to under 100 ppm]. The mixture was then heated to 90° C. (bath temperature). The addition funnel was charged with a solution of DPPA (3.80 g, 3 mL, 13.8 mmol) in toluene (25 mL). The DPPA solution was added over a 4-hour period and the mixture was allowed to stir for an additional 6 hours after complete addition. The solvent removed under reduced pressure and the crude oil was dissolved in 200 mL MTBE and added to a 500-mL separatory funnel. The organic phase was first washed 50 mL 5% citric acid and the layers cut. The organic phase was then washed with 50 mL sat. aq. $NaHCO_3$ and the layers cut. The organics were then washed with 50 mL $H_2O$ and the layers cut. Finally the organics were washed with 50 mL sat. aq. NaCl and the layers cut. The organic phase was dried over $MgSO_4$, filtered, and concentrated to provide a tan solid. The solid was crystallized from a minimal amount of heptane (~15 mL) to provide 3.2 g of a white crystalline solid (~3% of the symmetrical urea by-product was contained in this material). [Note: The urea by-product can be removed by passing the mixture through a 15-g plug of silica gel eluting with 25% EtOAc in hexanes. This provided 3.06 g of the product as a white crystalline solid.]

Alternate Stage 4. Curtius Rearrangement (Mixed Anhydride)

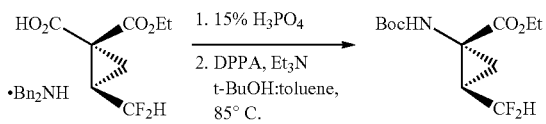

1. Salt Break:

A 500-mL round bottom flask, equipped with a teflon coated magnetic stirbar, was charged with the above dibenzyl amine salt (10.85 g, 26.8 mmol) and MTBE (100 mL). To this suspension was added a 15% $H_3PO_4$ solution (w/w, 100 mL) and the resulting mixture was stirred at room temperature for 20 min. The resulting solution was poured into a 250-mL separatory funnel and the layers were cut. The top organic layer was washed with an additional 50 mL 15% $H_3PO_4$ and the layers cut. The organic layer was then washed with sat. aq. NaCl, the layers cut, and the organics dried over $MgSO_4$. After filtration of the $MgSO_4$, the solvent was removed in vacuo.

2. Mixed Anhydride Formation:

The resulting oil was charged to a 250-mL round bottom flask, equipped with a teflon coated magnetic stirbar. To the residue was added dry acetone (55 mL) and triethylamine (5.6, 4.1 g, 40.2 mmol) followed by ethyl chloroformate (3.9 mL, 4.4 g, 40.2 mmol) at 0° C. over 10 min. The resulting mixture was stirred at 0° C. for 1 h. After this time, sodium azide (4.36 g, 67.0 mmol) in 45 mL $H_2O$ was added at 0° C. over 15 min. The mixture was stirred at this temperature for an additional 30 min. Toluene (110 mL) and water (110 mL) were added and the mixture poured into a 500 mL separatory funnel. The layers were cut and the top organic layer was washed with water (50 mL) and sat. aq. NaCl (50 mL). The organic phase was dried over $MgSO_4$, filtered, and concentrated under reduced pressure. The resulting oil was azeotropically dried with toluene by adding 25 mL of toluene and removing the solvent via rotary evaporation (3×25 mL toluene).

3. Curtius Rearrangement:

A separate three-necked 500-mL round bottom flask, equipped with a teflon coated magnetic stirbar, reflux condenser, and pressure equalizing addition funnel was charged with toluene (90 mL) and tert-butanol (90 mL) and was set to reflux (bath temp=85° C.). The solution of the acyl azide in 54 mL toluene was charged to the addition funnel and added to the refluxing solution of toluene:tert-butanol over 30 min. The solution was held at reflux for 10 h before cooling to room temperature. The solvent was removed under reduced pressure and the resulting oil was dissolved in 10:1 heptane:MTBE (25 mL) at room temperature. This solution was seeded with 500 mg of authentic material and allowed to sit at room temperature for 30 min. At this point, the mixture containing the precipitated product was cooled to 0° C. and allowed to stand for an additional 30 min. The product was collected by vacuum filtration and the solid washed with 50 mL ice-cold heptane. The solids were dried under vacuum to provide 5.6 g (75% yield) of the desired compound as a white solid.

Alternate Stage 4. Curtius Rearrangement (DPPA, 2 Mmol Scale)

A 25-mL round bottom flask, equipped with a teflon coated magnetic stirbar and reflux condenser, was charged with the mono-acid (435 mg, 2.09 mmol), tert-butanol (5 mL), and 4-Å molecular sieves (2.00 g, 1 g/mmol, powdered). The mixture was stirred for 15 min followed by addition of triethylamine (317 mg, 0.437 mL, 3.13 mmol) and diphenyl phosphorazidate (575 mg, 0.45 mL, 2.09 mmol). The reaction mixture was placed in an oil bath, preheated to 90° C. (bath temp). The mixture was stirred at this temperature for 10 h. At this point, the molecular sieves were filtered from the reaction (washing with 10 mL toluene). The volatiles were removed under reduced pressure and the remaining residue dissolved in diethyl ether (25 mL). The organic layer was washed with 5% aqueous citric acid (15 mL), sat. aq. sodium bicarbonate (15 mL), and sat. aq. sodium chloride (15 mL). The organics were dried over $MgSO_4$, filtered, and concentrated under reduced pressure to provide a pale yellow oil [Note: the material does not require purification at this point and can be subjected directly to ester hydrolysis]. Purification of the crude oil on silica gel (25 g) eluting with 25% EtOAc in hexanes provided 409 mg (70% yield) of the desired compound as a clear oil, which solidified upon standing.

Example 4

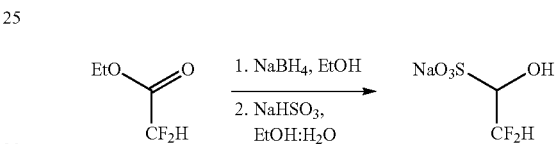

A 1-L three-necked flask equipped with a mechanical stirrer and addition funnel was charged with ethanol (200 mL) and ethyl difluoroacetate (25 g, 21.2 mL, 201 mmol). The flask was placed in a pre-cooled −20° C. bath. The solution was held at this temperature for 30 min. Sodium borohydride (7.5 g, 198 mmol) was added in three 2.5 g portions over 1.5 h (additions were at 30 min intervals). Upon complete addition, the mixture was stirred for an additional 1 h ($^1$H-NMR analysis indicated complete conversion) [Note: 1-mL aliquots were sampled from the reaction and quenched with 1 mL 1 N HCl at −78° C. The solutions were then diluted with diethyl ether (5 mL). The organic phase was removed with a pipet and evaporated to ~1 mL. 0.25 mL of the ethanol solution was added to the NMR tube diluted with 1 mL $CDCl_3$]. At this point, the addition funnel was charged with 1 N HCl (200 mL) and dropwise addition was started. The addition was complete within 30 min and the mixture was allowed to warm to 0° C. The mixture was diluted with diethyl ether (500 mL) and poured into a 2-L separatory funnel. The phases were cut and the organic phase washed with brine (250 mL). The organics were dried over $MgSO_4$, filtered, and concentrated under reduced pressure (0° C. bath temp, 150 mm Hg) to a volume of ~200 mL.

The ethanol solution was transferred to a 1-L round bottom flask equipped with a teflon coated magnetic stirbar and addition funnel. The addition funnel was charged with a solution of $NaHSO_3$ (20.97 g, 201 mmol) in 100 mL $H_2O$. The sodium bisulfite solution was added over 30 min and the mixture was allowed to stir for 24 h at which point the solvent and water were removed under reduced pressure producing a white solid. To the solid was added 100 mL ethanol and the mixture was gently heated to 50° C. (with swirling) to remove the product from the walls of the flask. The solids were filtered and washed with 200 mL hexanes to give a white powder. After drying under vacuum 23.4 g of the bisulfite adduct were obtained corresponding to a 63% yield.

Example 5

Triethoxytitanium(IV) Chloride:
A 250-mL round bottom flask, equipped with a teflon coated magnetic stirbar and a reflux condenser was charged with heptane (100 mL), tetraethoxytitanium (21.76 g, 20 mL, 95 mmol, 99.9% purity), and acetyl chloride (7.5 g, 6.8 mL, 95 mmol). The mixture was heated at reflux (bath temp 100° C.) for 90 min producing a yellow solution. The solution was cooled to room temperature and the reflux condenser was replaced with a short-path distillation apparatus. The bath temperature was increased to 130° C. and the heptane was allowed to distill from the pot. After removal of the solvent, the distillation apparatus was carefully placed under vacuum (~0.1 mm Hg) and the bath temperature increased to 180° C. The product distilled at 140° C. to give a viscous yellow oil (15.3 g, 73% yield).

Example 6—Asymmetric Synthesis of 1 Using Ellman's Auxiliary

Since its introduction in the late nineties, enantiopure tert-butanesulfinamide has shown widespread utility as a versatile chiral auxiliary. Condensation of tert-butanesulfinamide with aldehydes and ketones proceeds under mild conditions and provides activated imines that can participate in a number of highly diastereoselective reactions. Subsequent removal of the tert-butanesulfinyl group proceeds under mild conditions to reveal amine products.

Enantiopure tert-butanesulfinamide (Ellman's chiral auxiliary) may be used to construct a cyclopropyl amino acid (Scheme 2).

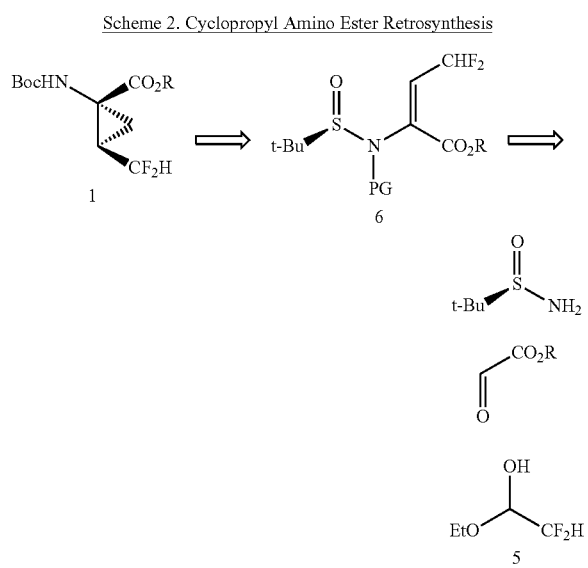

The synthesis of the glycine unit derived from Ellman's chiral auxiliary began with condensation of enantioenriched tert-butanesulfinamide and ethyl glyoxylate in the presence of a water scavenger, such as MgSO₄, to provide imine 2. Subsequent reduction of the imine with sodium borohydride, e.g., at 0° C., provided glycine 3 (for example, as shown in Scheme 3).

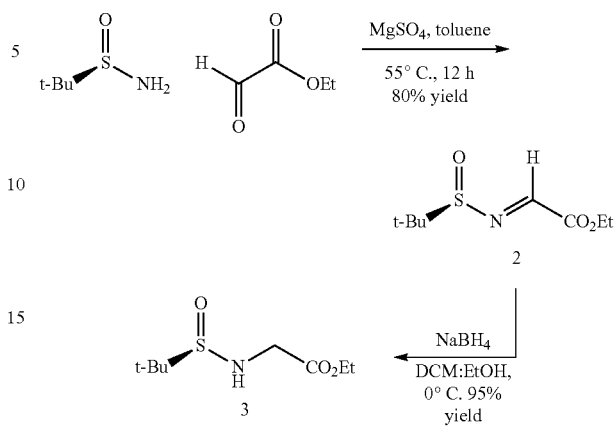

The amine was protected with a group that is readily cleaved under conditions that cleave the sulfinyl group; carbamates (e.g., tert-butyloxycarbonyl (Boc)) and ether (e.g., methoxymethyl (MOM)) based protecting groups were synthesized. Protection as the Boc derivative was performed by reacting the sulfonamide 3 with a Boc source (e.g., Boc₂O or BocCl) in the presence of 4-dimethylaminopyridine (DMAP) in a solvent such as acetonitrile (Table 1, entry 3).

TABLE 1

Evaluation of Protecting Groups

| Entry | Conditions | Solvent | Yield |
|---|---|---|---|
| 1 | Boc₂O, n-Buli | THF | 25% |
| 2 | Boc₂O, NaH | THF | 15% |
| 3 | Boc₂O, DMAP | MeCN | 95% |
| 4 | MOM-Cl, n-BuLi | THF | 0% |
| 5 | MOM-Cl, NaH | THF | 0% |
| 6 | MOM-Cl, DMAP | MeCN | 33% |

A Horner-Wadsworth-Emmons olefination combined the glycine-derived phosphonate 7 and difluoromethyl hemiacetal 5 into enoate 8 (such as depicted in Scheme 4). However, the undesired olefin isomer predominated, as confirmed by 2-D nuclear magnetic resonance (NMR) analysis.

Scheme 4. Olefination Reaction with 5

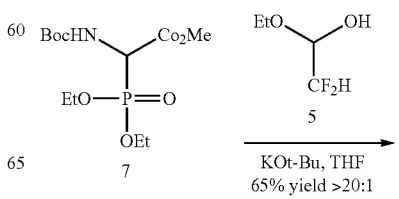

-continued

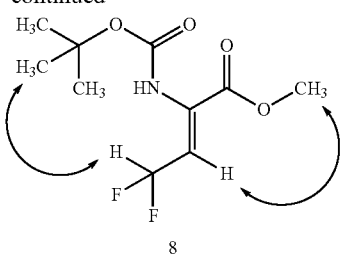
8

So, a similar phosphonate that would incorporate the chiral auxiliary from Ellman's amine was designed and prepared. Phosphonate 9 was prepared by condensation of Ellman's amine and ethyl glyoxylate. Lithium hexamethyldisilazane (LiHMDS) was used at low temperature in tetrahydrofuran (THF), which provides 9 in 54% yield (Table 2, entry 3).

TABLE 2

Synthesis of Chiral Phosphonate 9

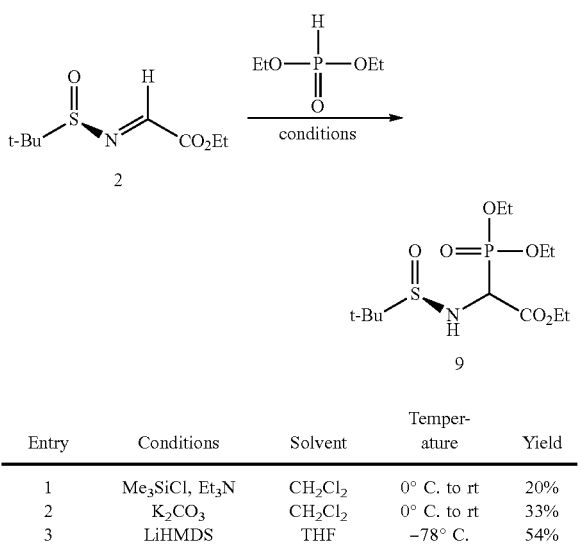

| Entry | Conditions | Solvent | Temperature | Yield |
|---|---|---|---|---|
| 1 | Me₃SiCl, Et₃N | CH₂Cl₂ | 0° C. to rt | 20% |
| 2 | K₂CO₃ | CH₂Cl₂ | 0° C. to rt | 33% |
| 3 | LiHMDS | THF | −78° C. | 54% |

Finally, olefin 10 was prepared. Without optimization, 10 was produced in 29% yield (olefin geometry was not determined) using KOt-Bu as the base (Scheme 5).

Scheme 5. Olefination with phosphonate 9

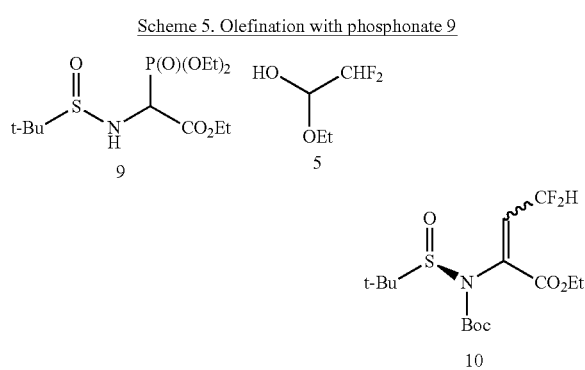

INCORPORATION BY REFERENCE

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents, and published patent applications, and patent applications cited throughout this application are incorporated herein by reference.

We claim:

1. A compound, or a salt thereof, having a structure selected from:

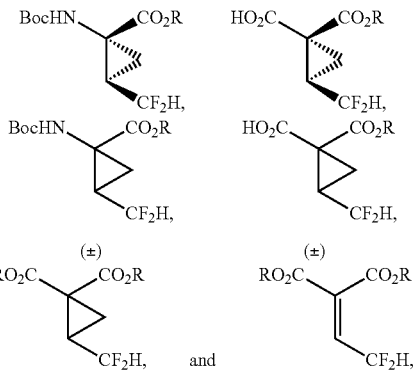

wherein, independently for each occurrence,
R is ethyl or n-propyl.

2. The compound of claim 1, wherein the compound is

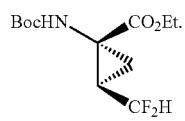 [SMILES: CCOC(=O)[C@@]1(NC(=O)OC(C)(C)C)C[C@H]1C(F)F]

3. The compound of claim 1, wherein the compound is selected from

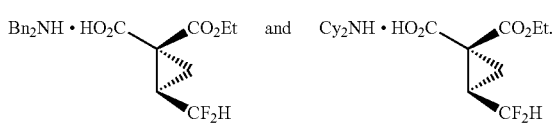

4. The compound of claim 1, wherein the compound is

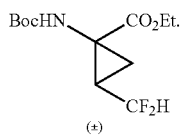

5. The compound of claim 1, wherein the compound is selected from

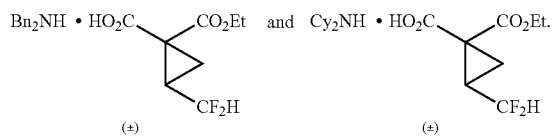

6. The compound of claim 1, wherein the compound is

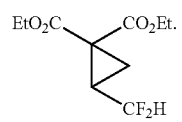

7. The compound of claim 1, wherein the compound is

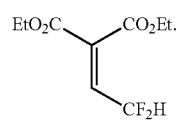

8. A method comprising any one of steps (i)-(vi), or a combination thereof:
(i)
contacting, in an eighth solvent, a compound of formula I with a fifth base, thereby forming a compound of formula J;
wherein
formula I is

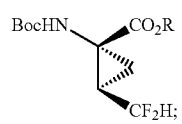

formula J is

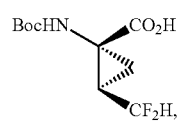

or a salt thereof; and
R is ethyl or n-propyl;
(ii)
subjecting a compound of formula F to simulated moving bed chromatography, thereby obtaining the enantioenriched compound of formula I;

wherein
formula F is

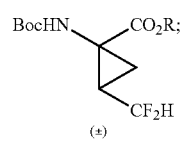

formula I is

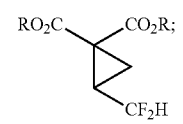

R is alkyl;
(iii)

Scheme A

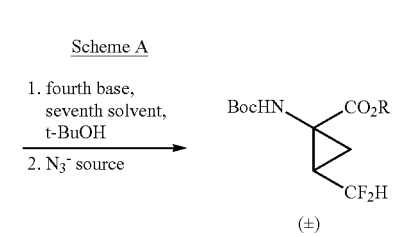

wherein R is alkyl;
(iv)
selectively hydrolyzing with a first enzyme the 2S-enantiomer of a compound of formula D, thereby forming a fourteenth product mixture;
separating from the fourteenth product mixture an enantioenriched amount of the 2R-enantiomer of a compound of formula D, thereby forming a fifteenth product mixture comprising an enantioenriched compound of formula G;
regioselectively hydrolyzing with a second enzyme the compound of formula G, thereby forming a sixteenth product mixture comprising a compound of formula H,
wherein
formula D is

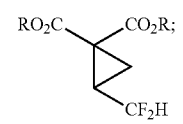

formula G is

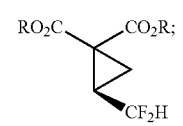

formula H is

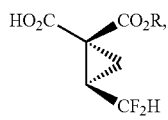

or a salt thereof; and
R is alkyl;
(v)

Scheme B

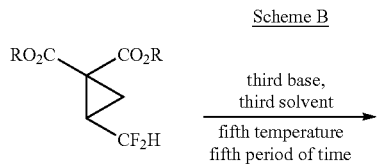

wherein R is alkyl; or
(vi)
heating a compound of formula C and trimethylsulfoxonium iodide in the presence of a second base and a second solvent at a fourth temperature for a fourth period of time, thereby forming a third product mixture comprising a compound of formula D,
wherein
formula C is

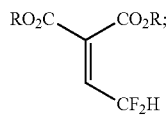

formula D is

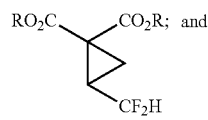

R is ethyl or n-propyl.

9. A compound, or a salt thereof, having a structure

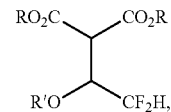

wherein, independently for each occurrence,
R is alkyl; and
R' is alkyl.

10. The compound of claim 9, wherein R is lower alkyl.
11. The compound of claim 9, wherein R is ethyl.
12. The compound of claim 9, wherein R is propyl.
13. The compound of claim 9, wherein R is isopropyl.
14. The compound of claim 9, wherein R' is ethyl, propyl, or isopropyl.
15. The compound of claim 9, wherein the compound is selected from

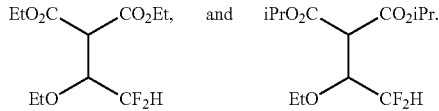

* * * * *